(12) United States Patent
Burgess et al.

(10) Patent No.: US 9,403,760 B2
(45) Date of Patent: Aug. 2, 2016

(54) COMPOUNDS

(71) Applicant: Avanti Polar Lipids, Inc., Alabaster, AL (US)

(72) Inventors: Stephen W Burgess, Chelsea, AL (US); Walter A Shaw, Birmingham, AL (US); Shengrong Li, Birmingham, AL (US)

(73) Assignee: AVANTI POLAR LIPIDS, INC., Alabaster, AL (US)

( * ) Notice: Subject to any disclaimer, the term of this patent is extended or adjusted under 35 U.S.C. 154(b) by 184 days.

(21) Appl. No.: 13/828,479

(22) Filed: Mar. 14, 2013

(65) Prior Publication Data

US 2014/0275591 A1   Sep. 18, 2014

(51) Int. Cl.
*C07C 271/22* (2006.01)
*C07C 229/22* (2006.01)

(52) U.S. Cl.
CPC ............ *C07C 271/22* (2013.01); *C07C 229/22* (2013.01); *Y02P 20/582* (2015.11)

(58) Field of Classification Search
None
See application file for complete search history.

(56) References Cited

U.S. PATENT DOCUMENTS 5,220,043 A * 6/1993 Dong et al. ............... 554/82
7,799,941 B2 * 9/2010 Hamada et al. ........... 560/42

OTHER PUBLICATIONS

Schmidt, U. et al., Syntheis of alpha-amino-beta-oxo acid esters, 1993, Synthesis, vol. 8, pp. 765-766 1 page abstract.*

Krysan, D., A rpatical synthesis of alpha-acylamino-beta-keto-esters, 1996, Tetrahedron Letters, vol. 37, No. 19, pp. 3303-3306.*

Hara, O., et al., Novel N—C acryol migration reaction of acyclic imides: A vacile method for alpha-aminoketones and beta-amino alcohols, 1998, Tetrahedron Letters, vol. 39, pp. 5537-5540.*

Goujon, J-Y, et al., Concise route to alpha-acylamino-beta-keto amides: application to the synthesis of a simplified azinomycin A Analogue, 2002, Tetrahedron Letters, vol. 43, pp. 9573-9576.*

Hartley, J.A., et al., A synthetic azinomycin analogue with demonstrated DNA cross-linking activity: Insights into the mechanism of actin of this class of antitumor agent, 2000, Angew. Chem, vol. 112, No. 19, pp. 3609-3612.*

Jung, Da Won "International Search Report—International application No. PCT/US2014/029298" Korean Intellectual Property Office; Jul. 29, 2014; pp. 1-3.

Turel, et al. "Sphingolipids; Part I—Synthesis of dl-erythro-1,3-Dihydroxy-2-dichloroacetamido-tetradecane" Indian J. Chem., vol. 17B, Apr. 1979, pp. 402-404.

Mordant, Celine, et al. "A Versatile Route to syn- and ant i-a-Amino-B-Hydroxy Esters from B-Keto Esters by Dynamic Kinetic Resolution with Ru-SYNPHOS Catalyst" Eur. J. Org. Chem. 2004, pp. 3017-3026.

* cited by examiner

*Primary Examiner* — Yate K Cutliff
(74) *Attorney, Agent, or Firm* — Thomas G. Peterson; Bradley Arant Boult Cummings LLP

(57) ABSTRACT

Disclosed are compounds of the general formula I and II (as further defined herein) are useful in the production of inhibitors of sphingolipid synthesis the production of sphingolipids. Suitable sphingolipids, include, but not limited to, sphingosine and compounds incorporating sphingosine or that may use sphingosine as an intermediate or a starting material in their synthesis (including, but not limited to, sphingosine-1-P, ceramide, gangliosides and sphingomyelin). In one contemplated use, compounds of the general formula I and II are useful in the production of sphingosine. In another contemplated use, compounds of the general formula I and II are useful in the production of a sphingofugin. Methods of manufacturing each of the above compounds are also provided.

16 Claims, No Drawings

COMPOUNDS

FIELD OF THE DISCLOSURE

The present disclosure related to compounds of the formula I and II. The use of these compounds in the preparation of certain lipids is also described.

BACKGROUND

Lipids are a diverse and ubiquitous group of compounds which have many key biological functions, such as acting as structural components of cell membranes, serving as energy storage sources and participating in signaling pathways. In addition to functions such as providing cellular structure, energy storage and cellular transport, the role of lipid molecules in a variety of cell signaling pathways has also been the focus of recent research.

Lipid signaling may occur via activation of a variety of receptors, including G protein-coupled and nuclear receptors, and members of several different lipid categories have been identified as signaling molecules and cellular messengers. There are many examples of important signaling lipids including sphingosine-1-phosphate, a sphingolipid derived from ceramide that is a potent messenger molecule involved in regulating calcium mobilization, cell growth, and apoptosis, diacylglycerol and the inositol phosphates derived from the phosphatidylinositolphosphates, involved in calcium-mediated activation of protein kinase C as well as the prostaglandins, which are one type of fatty-acid derived eicosanoid involved in inflammation and immunity.

One class of molecules currently being investigated for therapeutic activity includes the sphingolipids, such as sphingosine-1-P, sphingosine, ceramide, gangliosides and sphigomyelin.

In addition to potential as a therapeutic agent in and of itself, sphingosine can be used as a starting material in the synthesis of a variety of sphingolipids, including, but not limited to, sphingosine-1-P, ceramide, gangliosides and sphigomyelin.

Current synthetic methods for the production of various sphingolipids are currently not suitable for large scale production. To realize the potential for various lipid molecules as therapeutics, it is essential that the lipid molecules be available in a highly purified form and in quantities and price points compatible for use in pharmaceutical products. Such issues also apply to certain inhibitors of sphingolipid synthesis, which are structurally related to various intermediates in sphingolipid production. Therefore, the art is lacking synthetic methods for the economical production of sphingolipids and inhibitors of sphingolipid synthesis.

The present disclosure provides a series of compounds useful in the production of sphingolipids, such as, but not limited to, sphingosine and compounds incorporating sphingosine (including, but not limited to, sphingosine-1-P, ceramide, gangliosides and sphigomyelin) as well as compounds useful as inhibitors of sphingolipid synthesis.

SUMMARY OF THE DISCLOSURE

In a first aspect, the present disclosure provides compounds of the formula I:

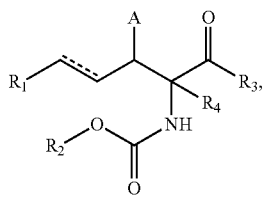

wherein the variables are as defined below.

In a second aspect, the present disclosure provides compounds of the formula II:

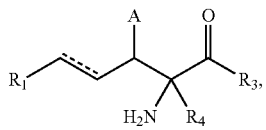

wherein the variables are as defined below.

Compounds of the first and second aspects are useful in the production of inhibitors of sphingolipid synthesis and in the production of sphingolipids. Suitable sphingolipids, include, but not limited to, sphingosine and compounds incorporating sphingosine or that may use sphingosine as an intermediate or a starting material in their synthesis (including, but not limited to, sphingosine-1-P, ceramide, gangliosides and sphigomyelin). In one embodiment, compounds of the first and second aspects are useful in the production of sphingosine. In one embodiment, compounds of the first and second aspects are useful in the production of a sphingofugin.

In a third aspect, the present disclosure provides methods for manufacturing a sphingolipid. In one embodiment of this aspect, the method of manufacture comprise providing a compound of the general formula I, performing a series of chemical transformations on the compound of the general formula I to arrive at a sphingolipid. In another embodiment of this aspect, the method of manufacture comprise providing a compound of the general formula II, performing a series of chemical transformations on the compound of the general formula II to arrive at a sphingolipid.

In a fourth aspect, the present disclosure provides methods for manufacturing an inhibitor of sphingolipid synthesis. In one embodiment of this aspect, the method of manufacture comprise providing a compound of the general formula I, performing a series of chemical transformations on the compound of the general formula I to arrive at an inhibitor of sphingolipid synthesis. In another embodiment of this aspect, the method of manufacture comprise providing a compound of the general formula II, performing a series of chemical transformations on the compound of the general formula II to arrive at an inhibitor of sphingolipid synthesis.

DETAILED DESCRIPTION

Definitions

As used herein, the term "protected" with respect to hydroxyl groups, amine groups, sulfhydryl groups and other reactive groups refers to forms of these functionalities which are protected from undesirable reaction with a protecting group known to those skilled in the art such as those set forth in Protective Groups in Organic Synthesis, Greene, T. W.; Wuts, P. G. M., John Wiley & Sons, New York, N.Y., (3rd Edition, 1999), Enzymatic Catalyis in Organic Synthesis (2ed edition, Drauz K. and Waldemann, H., Eds; Wiley-VCH: Weinheim; 2002), Preparative Biotransformations (Roberts S. et al., J. Chem Society, Perkin Trans I, p 1475-1499, 2001), Enhancement of Selectivity and Reactivity of Lipases by Additives (Theil, F., Tetrahedron, vol. 56, p 2905, 2000), Lipases: Interfacial Enzymes with Attractive Applications (Schmid, R., et al., Angew. Chem. Int. Ed, vol. 37, p 1609, 1998), Biotransformations in the Synthesis of Enantiopure Bioactive Molecules (Johnson, C. R., Acc. Chem. Res., vol. 31, p 333, 1998), synthesis and Modification of Carbohydrates Using Glycosidases and Lipases (Fernandez-Mayoralas, Top. Curr. Chem, vol 186, p 1, 1997), O,N-Acetale (Rasshofer, W., in Carbonyl Derivative 1, Teil 2, Hagemann, H and Klamann, D. Eds, Houben-weyl, $4^{th}$ ed., Vol 14a/2, Thieme: Stuttgart, 1991), Reduction of C+N to CH—NH by Metal Hydrides (Hutchins, R. et al., Comp. Oran. Synth., vol 8, p 25, 1991) Esters of Carbamic Acid (Adams, P. et al., Chem. Rev. vol 89, p 689, 1989), The Gabriel Synthesis of Primary Amines (Gibson M. S, et al., Angew. Chem. Int. Ed. Engl, vol 7, p 919, 1968) and Protecting Groups ($3^{rd}$ ed., ISBN 9781588903761) which can be added or removed using the procedures set forth therein (each of the foregoing references is incorporated herein in its entirety for such teachings).

Examples of protecting groups for use with hydroxyl groups include, but are not limited to, silyl ethers (including, but not limited to, trimethylsilyl ethers, triethylsilyl ethers, tert-butyldimethylsilyl ethers, tert-butyldiphenylsilyl ethers, triisopropylsilyl ethers, diethylisopropylsilyl ethers, thexyldimethylsilyl ethers, triphenylsilyl ethers and di-tert-butylmethylsilyl ethers), alkyl ethers (including, but not limited to, methyl ethers, tert-butyl ethers, benzyl ethers, p-methoxybenzyl ethers, 3,4-di-methoxybenzyl ethers, trityl ethers, ally ethers and allyloxycarbonyl derivatives), alkoxymethyl ethers (including, but not limited to, methoxymethyl ethers, 2-methoxyethoxymethyl ethers, benzyloxymethyl ethers, p-methoxybenzyloxymethyl ethers and 2-(trimethylsilyl) ethoxymethyl ethers), tetrahydropyranyl ethers, methylthiomethyl ethers, esters (including, but not limited to, acetate esters, benzoate esters, pivalate esters, methoxyacetate esters, chloroacetate esters and levulinate esters) and carbonates (including, but not limited to, benzy carbonates, p-nitrobenzyl carbonates, tert-butyl carbonates, 2,2,2-trichloroethyl carbonates). Examples of protecting groups for use with amino groups include, but are not limited to, imides and amides (including, but not limited to, phthaloyl, tetrachlorophtaloyl, dithiasuccinyl, trifluoroacetyl, and relay deprotection of N-acyl derivatives), carbamates (including, but not limited to, methoycarbonyl, ethoxycarbonyl, tert-butoxycarbonyl, benzyloxycarbonyl, allyloxycarbonyl, 9-fluorenylmethoxycarbonyl and 2,2,2-tricloroethoxycarbonyl), sulfonyl derivatives (including, but not limited to, arylsulfonyl derivatives and 2-(trimethylsilyl)ethylsulfonyl), N-sulfenyl derivatives, N-alkyl derivatives (including, but not limited to, N,O-acetals, triazinanones, benzylmethyl, diphenylmethyl, tritylfluorenyl, phenylfluoroenyl and allyl groups) and N-silyl derivatives (including, but not limited to, imine derivatives, enamine derivatives, N-Bis(methylthio)methylene and N-diphenylmethylene)

As used herein, the term "alkyl", whether used alone or as part of a substituent or linking group, includes straight hydrocarbon groups comprising from one to twenty carbon atoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$) CH$_2$CH(CH$_3$)$_2$, —CH(CH$_3$)CH(CH$_3$)CH(CH$_3$)CH(CH$_3$)$_2$, —CH(CH$_2$CH$_3$)CH(CH$_3$)CH(CH$_3$)(CH$_2$CH$_3$), and others. The phrase also includes cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and such rings substituted with straight and branched chain alkyl groups as defined above.

As used herein, the term "alkylene", whether used alone or as part of a substituent group, includes any group obtained by removing a hydrogen atom from an alkyl group; an alkylene group forms two bonds with other groups.

As used herein, the term "alkenyl", whether used alone or as part of a substituent group, includes an alkyl group having at least one double bond between any two adjacent carbon atoms.

As used herein, the term "alkynyl", whether used alone or as part of a substituent group, includes an alkyl group having at least one triple bond between any two adjacent carbon atoms.

As used herein, the term "unsubstituted alkyl", "unsubstituted alkenyl", and "unsubstituted alkynyl" refers to alkyl, alkenyl and alkynyl groups that do not contain heteroatoms.

The phrase "substituted alkyl", "substituted alkenyl", and "substituted alkynyl" refers to alkyl, alkenyl and alkynyl groups as defined above in which one or more bonds to a carbon(s) or hydrogen(s) are replaced by a bond to non-hydrogen or non-carbon atoms such as, but not limited to, a halogen atom in halides such as F, Cl, Br, and I; and oxygen atom in groups such as carbonyl, carboxyl, hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, enamines imines, oximes, hydrazones, and nitriles; a silicon atom in groups such as in trialkylsilyl groups, dialkylarylsilyl groups, alkyldiarylsilyl groups, and triarylsilyl groups; and other heteroatoms in various other groups. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl) (heterocyclyl)-amine, (aryl)(heterocyclyl)amine, or diheterocyclylamine group.

As used herein, the term "unsubstituted aryl" refers to monocyclic or bicyclic aromatic hydrocarbon groups having 6 to 12 carbon atoms in the ring portion, such as, but not limited to, phenyl, naphthyl, anthracenyl, biphenyl and diphenyl groups, that do not contain heteroatoms. Although the phrase "unsubstituted aryl" includes groups containing condensed rings such as naphthalene, it does not include aryl groups that have other groups such as alkyl or halo groups bonded to one of the ring members, as aryl groups such as tolyl are considered herein to be substituted aryl groups as described below. Unsubstituted aryl groups may be bonded to one or more carbon atom(s), oxygen atom(s), nitrogen atom(s), and/or sulfur atom(s) in the parent compound, however.

As used herein, the term "substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms, such as, but not limited to, those atoms described above with respect to a substituted alkyl, and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g. dihydronaphthyl or tetrahydronaphthyl). Thus, the phrase "substituted aryl" includes, but is not limited to tolyl, and hydroxyphenyl among others.

As used herein, the term "unsubstituted aralkyl" refers to unsubstituted or substituted alkyl, alkenyl or alkynyl groups as defined above in which a hydrogen or carbon bond of the unsubstituted or substituted alkyl, alkenyl or alkynyl group is replaced with a bond to an aryl group as defined above. For example, methyl ($CH_3$) is an unsubstituted alkyl group. If a hydrogen atom of the methyl group is replaced by a bond to a phenyl group, such as if the carbon of the methyl were bonded to a carbon of benzene, then the compound is an unsubstituted aralkyl group (i.e., a benzyl group).

As used herein, the term "substituted aralkyl" has the same meaning with respect to unsubstituted aralkyl groups that substituted aryl groups had with respect to unsubstituted aryl groups. For example, methyl ($CH_3$) bound to a phenyl group, wherein the phenyl group is substituted (for example b a hydroxy group), the compounds is a substituted aralkyl. However, a substituted aralkyl group also includes groups in which a carbon or hydrogen bond of the alkyl part of the group is replaced by a bond to a non-carbon or a non-hydrogen atom.

As used herein, the term "unsubstituted heterocyclyl" refers to both aromatic and nonaromatic ring compounds including monocyclic, bicyclic, and polycyclic ring compounds such as, but not limited to, quinuclidyl, containing 3 or more ring members of which one or more is a heteroatom such as, but not limited to, N, O, and S. Although the phrase "unsubstituted heterocyclyl" includes condensed heterocyclic rings such as benzimidazolyl, it does not include heterocyclyl groups that have other groups such as alkyl or halo groups bonded to one of the ring members, as compounds such as 2-methylbenzimidazolyl are "substituted heterocyclyl" groups as defined below. Examples of heterocyclyl groups include, but are not limited to: unsaturated 3 to 8 membered rings containing 1 to 4 nitrogen atoms such as, but not limited to pyrrolyl, pyrrolinyl, imidazolyl, pyrazolyl, pyridyl, dihydropyridyl, pyrimidyl, pyrazinyl, pyridazinyl, triazolyl, tetrazolyl; saturated 3 to 8 membered rings containing 1 to 4 nitrogen atoms such as, but not limited to, pyrrolidinyl, imidazolidinyl, piperidinyl, piperazinyl; condensed unsaturated heterocyclic groups containing 1 to 4 nitrogen atoms such as, but not limited to, indolyl, isoindolyl, indolinyl, indolizinyl, benzimidazolyl, quinolyl, isoquinolyl, indazolyl, benzotriazolyl; unsaturated 3 to 8 membered rings containing 1 to 2 oxygen atoms and 1 to 3 nitrogen atoms such as, but not limited to, oxazolyl, isoxazolyl, oxadiazolyl; saturated 3 to 8 membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxazolyl, benzoxadiazolyl, benzoxazinyl (e.g. 2H-1,4-benzoxazinyl etc.); unsaturated 3 to 8 membered rings containing 1 to 3 sulfur atoms and 1 to 3 nitrogen atoms such as, but not limited to, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.); saturated 3 to 8 membered rings containing 1 to 2 sulfur atoms and 1 to 3 nitrogen atoms such as, but not limited to, thiazolodinyl; saturated and unsaturated 3 to 8 membered rings containing 1 to 2 sulfur atoms such as, but not limited to, thienyl, dihydrodithiinyl, dihydrodithionyl, tetrahydrothiophene, tetrahydrothiopyran; unsaturated condensed heterocyclic rings containing 1 to 2 sulfur atoms and 1 to 3 nitrogen atoms such as, but not limited to, benzothiazolyl, benzothiadiazolyl, benzothiazinyl (e.g. 2H-1,4-benzothiazinyl, etc.), dihydrobenzothiazinyl (e.g. 2H-3,4-dihydrobenzothiazinyl, etc.), unsaturated 3 to 8 membered rings containing oxygen atoms such as, but not limited to furyl; unsaturated condensed heterocyclic rings containing 1 to 2 oxygen atoms such as benzodioxolyl (e.g. 1,3-benzodioxoyl, etc.); unsaturated 3 to 8 membered rings containing an oxygen atom and 1 to 2 sulfur atoms such as, but not limited to, dihydrooxathiinyl; saturated 3 to 8 membered rings containing 1 to 2 oxygen atoms and 1 to 2 sulfur atoms such as 1,4-oxathiane; unsaturated condensed rings containing 1 to 2 sulfur atoms such as benzothienyl, benzodithiinyl; and unsaturated condensed heterocyclic rings containing an oxygen atom and 1 to 2 oxygen atoms such as benzoxathiinyl. Heterocyclyl group also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include morpholine, piperazine, piperidine, pyrrolidine, imidazole, pyrazole, 1,2,3-triazole, 1,2,4-triazole, tetrazole, thiomorpholine, thiomorpholine in which the S atom of the thiomorpholine is bonded to one or more O atoms, pyrrole, homopiperazine, oxazolidin-2-one, pyrrolidin-2-one, oxazole, quinuclidine, thiazole, isoxazole, furan, and tetrahydrofuran.

As used herein, the term "substituted heterocyclyl" has the same meaning with respect to unsubstituted heterocyclyl groups that substituted alkyl groups had with respect to unsubstituted alkyl groups. However, a substituted heterocyclyl group also includes heterocyclyl groups in which one of the carbons is bonded to one of the non-carbon or non-hydrogen atom, such as, but not limited to, those atoms described above with respect to a substituted alky and substituted aryl groups and also includes heterocyclyl groups in which one or more carbons of the heterocyclyl group is bonded to a substituted and/or unsubstituted alkyl, alkenyl, alkynyl or aryl group as defined herein. This includes bonding arrangements in which two carbon atoms of an heterocyclyl group are bonded to two atoms of an alkyl, alkenyl, or alkynyl group to define a fused ring system. Examples, include, but are not limited to, 2-methylbenzimidazolyl, 5-methylbenzimidazolyl, 5-chlorobenzthiazolyl, 1-methyl piperazinyl, and 2-chloropyridyl among others.

As used herein, the term "unsubstituted heterocycloalkyl" refers to unsubstituted or substituted alkyl, alkenyl or alkynyl groups as defined above in which a hydrogen or carbon bond of the unsubstituted or substituted alkyl, alkenyl or alkynyl group is replaced with a bond to a heterocyclyl group as defined above. For example, methyl ($CH_3$) is an unsubstituted alkyl group. If a hydrogen atom of the methyl group is replaced by a bond to a heterocyclyl group, such as if the carbon of the methyl were bonded to carbon 2 of pyridine (one of the carbons bonded to the N of the pyridine) or carbons 3 or 4 of the pyridine, then the compound is an unsubstituted heterocycloalkyl group.

As used herein, the term "substituted heterocycloalkyl" has the same meaning with respect to unsubstituted heterocycloalkyl groups that substituted aryl groups had with respect to unsubstituted aryl groups. However, a substituted heterocycloalkyl group also includes groups in which a non-hydrogen atom is bonded to a heteroatom in the heterocyclyl group of the heterocycloalkyl group such as, but not limited to, a nitrogen atom in the piperidine ring of a piperidinylalkyl group.

Compounds

The present disclosure provides compounds of the formula I and II. Such compounds are useful in the production of sphingolipids, such as, but not limited to, sphingosine and compounds incorporating sphingosine or that may use sphingosine as an intermediate in their synthesis (including, but not limited to, sphingosine-1-P, ceramide, gangliosides and sphigomyelin). In one embodiment, compounds of the formula I and II are useful in the production of sphingosine. In an alternate embodiment, the sphingosine produced may be used in the production of other sphingolipids, such as, but not limited to, sphingosine-1-P, ceramide, gangliosides and sphigomyelin.

Compounds of the formula I have the following structure:

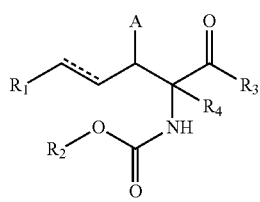
(I)

wherein:

A is a ketone group (=O) or A is $R_5$ and $R_6$, wherein $R_5$ is H or a substituted or unsubstituted alkyl, alkenyl or alkynyl group and $R_6$ is a OH group or a $OR_7$ group, wherein $R_7$ is a substituted or unsubstituted alkyl, a substituted or unsubstituted alkenyl, or a substituted or unsubstituted alkynyl group;

- - - - represents an optional double bond; for clarity the bond represented by - - - - may be present resulting in a double bond at the indicated position or it may be absent resulting in a single bond at the indicated position;

$R_1$ is a substituted or unsubstituted alkyl group or, a substituted or unsubstituted alkenyl group, a substituted or unsubstituted alkynyl group, or $(CH_2)_n$—$R_8$, where $R_8$ is a substituted or unsubstituted aryl, a substituted or unsubstituted aralkyl a substituted or unsubstituted heterocycle or a substituted or unsubstituted heterocycloalkyl;

$R_2$ is H, substituted or unsubstituted alkyl group or, a substituted or unsubstituted alkenyl group, a substituted or unsubstituted alkynyl group benzyl, or $(CH_2)_p$—$R_9$, where $R_9$ is a substituted or unsubstituted aryl, a substituted or unsubstituted aralkyl a substituted or unsubstituted heterocycle or a substituted or unsubstituted heterocycloalkyl;

$R_3$ is a protecting group;

$R_4$ is H, a substituted or unsubstituted alkyl, a substituted or unsubstituted aralalkyl, a substituted or unsubstituted heterocycloalkyl or a side chain group from any one of the naturally or non-naturally occurring amino acids; and n and p are each independently selected from 0-10.

Examples of various protecting groups are provided herein. In one embodiment, $R_3$ is a silyl ether, an alkyl ether, an alkoxymethyl ether, a tetrahydropyranyl ether, a methylthiomethyl ethers, an esters or a carbonate. In one embodiment, $R_3$ is an $OR_{10}$ group, wherein $R_{10}$ is a substituted or unsubstituted alkyl, a substituted or unsubstituted alkenyl group, a substituted or unsubstituted alkynyl group, a substituted or unsubstituted aryl, a substituted or unsubstituted aralkyl a substituted or unsubstituted heterocycle or a substituted or unsubstituted heterocycloalkyl. In a particular embodiment, when $R_{10}$ is a substituted or unsubstituted alkyl, a substituted or unsubstituted alkenyl group, a substituted or unsubstituted alkynyl group, such groups are from 1 to 6 carbons in length. In a particular embodiment, $R_3$ is an O—$CH_3$ group.

As discussed above, $R_4$ may be a side chain group from any one of the naturally or non-naturally occurring amino acids. As such the side group is defined to occupy the position R in the following structure In a specific embodiment, such side chain is selected from the group consisting of: —$CH_2(CH_2)_m(CH_3)(CH_3)$, —$CH(CH_3)(CH_2)_mCH3$, —$(CH_2)_mC(=O)(NH_2)$, —$(CH_2)_m COOH$, —$(CH_2)_mSCH_3$, —$(CH_2)_mOH$, —$CH(OH)(CH_2)_m CH_3$, —$(CH_2)_mSH$, $CH_2(CH_2)_mNH_2$, and —$CH_2(CH_2)_m NHC(NH_2)(NH_2)$, wherein m is an integer selected from 1-4 for each occurrence.

In a specific embodiment, such side chain is selected from the group consisting of: —$CH_3$, —$CH(CH_3)(CH_3)$, —$CH_2CH_2(CH_3)(CH_3)$, —$CH(CH_3)CH_2CH_3$, —$CH_2C(=O)(NH_2)$, $CH_2CH_2C(=O)(NH_2)$, —$CH_2COOH$, —$CH_2CH_2COOH$, —$CH_2CH_2SCH_3$, —$CH_2OH$, —$CH(OH)CH_3$, —$CH_2SH$, —$CH_2(CH_2)_3NH_2$, —$CH_2(CH_2)_2 NHC(NH_2)(NH_2)$,

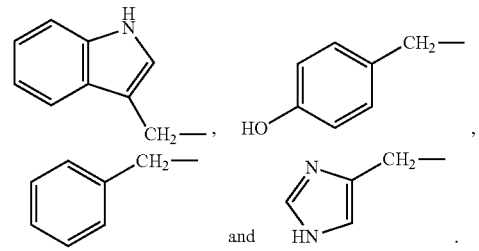

In a specific embodiment, such side chain is —$(CH_2)_mOH$, —$CH(OH)(CH_2)_mCH_3$, —$CH_2OH$ or —$CH(OH)CH_3$ wherein m is an integer selected from 1-4 for each occurrence.

In one embodiment of the foregoing, A is a ketone group and the compound has the formula Ia;

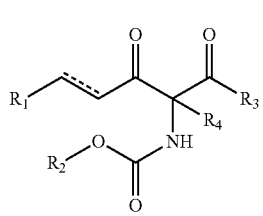
(Ia)

wherein:

$R_1$, $R_2$, $R_3$ and $R_4$ are as defined above for compounds of the formula I.

In one embodiment of the foregoing, A is $R_5$ and $R_6$, where $R_5$ is H and $R_6$ is OH and the compound has the formula Ib:

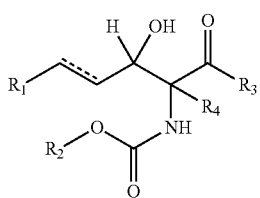
(Ib)

wherein:

$R_1$, $R_2$, $R_3$ and $R_4$ are as defined above for compounds of the formula I.

In a particular embodiment of compound I(b), the compound has the general formula represented in formula I(c) below. In certain embodiments, compounds of the formula I(c) are produced as intermediates in the synthesis of a sphingolipid.

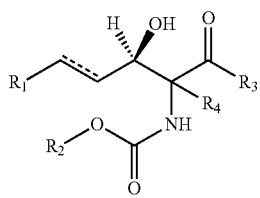
(Ic)

In a particular embodiment of the foregoing compound of the formula I, A is a ketone group, - - - - is present resulting in a double bond at the indicated position, $R_1$ is an unsubstituted $C_6$-$C_{14}$ alkyl, alkenyl or alkynyl group; $R_2$ is $CH_3$ or benzyl; $R_3$ is O—$CH_3$ and $R_4$ is H.

In another particular embodiment of the foregoing compound of the formula I, A is a ketone group, - - - - is absent resulting in a single bond at the indicated position, $R_1$ is an unsubstituted $C_6$-$C_{14}$ alkyl, alkenyl or alkynyl group; $R_2$ is $CH_3$ or benzyl, $R_3$ is O—$CH_3$ and $R_4$ is H.

In a particular embodiment of the foregoing compound of the formula I, A is a ketone group, - - - - is present resulting in a double bond at the indicated position, $R_1$ is a substituted $C_6$-$C_{14}$ alkyl, alkenyl or alkynyl group; $R_2$ is $CH_3$ or benzyl, $R_3$ is O—$CH_3$ and $R_4$ is H.

In another particular embodiment of the foregoing compound of the formula I, A is a ketone group, - - - - is absent resulting in a single bond at the indicated position, $R_1$ is a substituted $C_6$-$C_{14}$ alkyl, alkenyl or alkynyl group; $R_2$ is $CH_3$ or benzyl, $R_3$ is O—$CH_3$ and $R_4$ is H.

In a particular embodiment of the foregoing compound of the formula I, A is $R_5$ and $R_6$, where $R_5$ is H and $R_6$ is OH, - - - - is present resulting in a double bond at the indicated position, $R_1$ is an unsubstituted $C_6$-$C_{14}$ alkyl, alkenyl or alkynyl group; $R_2$ is $CH_3$ or benzyl; $R_3$ is O—$CH_3$ and $R_4$ is H.

In another particular embodiment of the foregoing compound of the formula I, A is $R_5$ and $R_6$, where $R_5$ is H and $R_6$ is OH, - - - - is absent resulting in a single bond at the indicated position, $R_1$ is an unsubstituted $C_6$-$C_{14}$ alkyl, alkenyl or alkynyl group; $R_2$ is $CH_3$ or benzyl, $R_3$ is O—$CH_3$ and $R_4$ is H.

In a particular embodiment of the foregoing compound of the formula I, A is $R_5$ and $R_6$, where $R_5$ is H and $R_6$ is OH, - - - - is present resulting in a double bond at the indicated position, $R_1$ is a substituted $C_6$-$C_{14}$ alkyl, alkenyl or alkynyl group; $R_2$ is $CH_3$ or benzyl, $R_3$ is O—$CH_3$ and $R_4$ is H.

In another particular embodiment of the foregoing compound of the formula I, A is $R_5$ and $R_6$, where $R_5$ is H and $R_6$ is OH, - - - - is absent resulting in a single bond at the indicated position, $R_1$ is a substituted $C_6$-$C_{14}$ alkyl, alkenyl or alkynyl group; $R_2$ is $CH_3$ or benzyl, $R_3$ is O—$CH_3$ and $R_4$ is H.

In another particular embodiment of the foregoing compound of the formula I, A is a ketone group, - - - - is present resulting in a double bond at the indicated position, $R_1$ is an unsubstituted $C_6$-$C_{14}$ alkyl, alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is present resulting in a double bond at the indicated position, $R_1$ is a substituted $C_6$-$C_{14}$ alkyl or alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is absent resulting in a single bond at the indicated position, $R_1$ is an unsubstituted $C_6$-$C_{14}$ alkyl, alkenyl or alkynyl; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is absent resulting in a single bond at the indicated position, $R_1$ is a substituted $C_6$-$C_{14}$ alkyl, alkenyl or alkynyl; $R_2$ is $CH_3$ or benzyl, $R_3$ is O—$CH_3$ and $R_4$ is $CH_2$—OH.

In another particular embodiment of the foregoing compound of the formula I, A is $R_5$ and $R_6$, where $R_5$ is H and $R_6$ is OH, - - - - is present resulting in a double bond at the indicated position, $R_1$ is an unsubstituted $C_6$-$C_{14}$ alkyl, alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is $R_5$ and $R_6$, where $R_5$ is H and $R_6$ is OH, - - - - is present resulting in a double bond at the indicated position, $R_1$ is a substituted $C_6$-$C_{14}$ alkyl or alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is $R_5$ and $R_6$, where $R_5$ is H and $R_6$ is OH, - - - - is absent resulting in a single bond at the indicated position, $R_1$ is an unsubstituted $C_6$-$C_{14}$ alkyl, alkenyl or alkynyl; $R_2$ is $CH_3$ or benzyl, $R_3$ is O—$CH_3$ and $R_4$ is $CH_2$—OH.

In another particular embodiment of the foregoing compound of the formula I, A is $R_5$ and $R_6$, where $R_5$ is H and $R_6$ is OH, - - - - is absent resulting in a single bond at the indicated position, $R_1$ is a substituted $C_6$-$C_{14}$ alkyl, alkenyl or alkynyl; $R_2$ is $CH_3$ or benzyl, $R_3$ is O—$CH_3$ and $R_4$ is $CH_2$—OH.

In one embodiment of the foregoing, $R_1$ is an unsubstituted $C_{10}$ alkyl group, $R_1$ is an unsubstituted $C_{11}$ alkyl group, $R_1$ is an unsubstituted $C_{12}$ alkyl group or $R_1$ is an unsubstituted $C_{13}$ alkyl group.

In one embodiment of the foregoing, $R_1$ is a substituted $C_{10}$ alkyl group, $R_1$ is a substituted $C_{11}$ alkyl group, $R_1$ is substituted $C_{12}$ alkyl group or $R_1$ is a substituted $C_{13}$ alkyl group.

In one embodiment of the foregoing, $R_1$ is an unsubstituted alkyl, alkenyl or alkynyl group from 1-25 carbons in length. In an alternate embodiment, $R_1$ is an unsubstituted alkyl, alkenyl or alkynyl group from 4-20 carbons in length. In an alternate embodiment, $R_1$ is an unsubstituted alkyl, alkenyl or alkynyl group from 6-18 carbons in length. In an alternate embodiment, $R_1$ is an unsubstituted alkyl, alkenyl or alkynyl group from 8-16 carbons in length.

In an alternate embodiment, $R_1$ is an unsubstituted alkyl, alkenyl or alkynyl group from 10-14 carbons in length. In an alternate embodiment, $R_1$ is an unsubstituted alkyl, alkenyl or alkynyl group of 11 carbons in length. In an alternate embodiment, $R_1$ is an unsubstituted alkyl, alkenyl or alkynyl group of 12 carbons in length. In an alternate embodiment, $R_1$ is an unsubstituted alkyl, alkenyl or alkynyl group of 13 carbons in length.

In one embodiment of the foregoing, $R_1$ is a substituted alkyl, alkenyl or alkynyl group from 1-25 carbons in length. In an alternate embodiment, $R_1$ is a substituted alkyl, alkenyl or alkynyl group from 4-20 carbons in length. In an alternate embodiment, $R_1$ is a substituted alkyl, alkenyl or alkynyl group from 6-18 carbons in length. In an alternate embodiment, $R_1$ is a substituted alkyl, alkenyl or alkynyl group from 8-16 carbons in length. In an alternate embodiment, $R_1$ is a substituted alkyl, alkenyl or alkynyl group from 10-14 carbons in length. In an alternate embodiment, $R_1$ is a substituted alkyl, alkenyl or alkynyl group of 11 carbons in length. In an alternate embodiment, $R_1$ is a substituted alkyl, alkenyl or alkynyl group of 12 carbons in length. In an alternate embodiment, $R_1$ is a substituted alkyl, alkenyl or alkynyl group of 13 carbons in length.

In one embodiment of the foregoing, when $R_1$ is a substituted or unsubstituted alkenyl group or alkynyl group, such group may have from 1-6 double or triple bonds. In one embodiment, such group has from 1-4 double or triple bonds; in another embodiment, such group has from 1-2 double or triple bonds; in another embodiment, such group has 1 double or triple bond. The double bonds may be in the cis or trans configuration. When multiple double bonds are present, the double bonds may be all cis, all trans or a combination of cis and trans. In one embodiment, when multiple double bonds are present, the double bonds are all cis or all trans.

In one embodiment of the foregoing, when a group, such as $R_1$, is a substituted alkyl group, alkenyl group or alkynyl group, the substituents for substitution include those listed herein with regard to the definition of a substituted alkyl group. In a particular embodiment, the substituents for substitution are —OH, —NH$_2$, N$_3$ or =O. When such group is substituted the number of substituent groups may vary from one to the number of carbon atoms in the substituted alkyl chain. In one embodiment, the number of substituent groups is from 1-6; in another embodiment, the number of substituent groups is from 1-8; in another embodiment, the number of substituent groups is from 1-4, in another embodiment, the number of substituent groups is from 1-2.

In a particular embodiment, compounds of the formula I have the following structure:

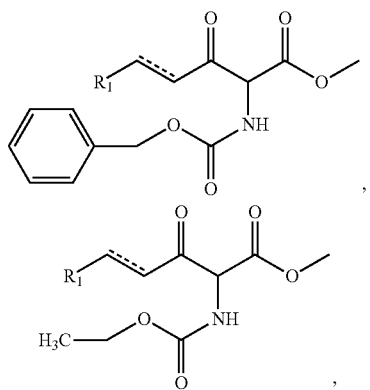

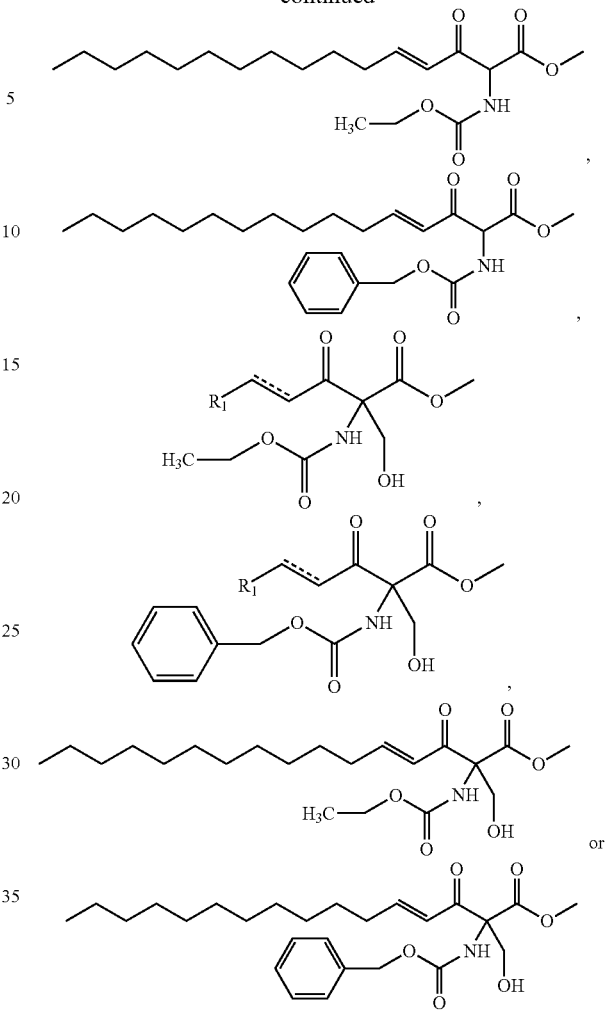

The present disclosure also provides for compounds of the formula II. Compounds of the formula II have the following structure:

(II)

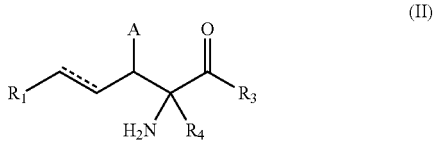

wherein:

A is a ketone group (=O) or A is $R_5$ and $R_6$, wherein $R_5$ is H or a substituted or unsubstituted alkyl, alkenyl or alkynyl group and $R_6$ is a OH group or a OR$_7$ group, wherein $R_7$ is a substituted or unsubstituted alkyl, a substituted or unsubstituted alkenyl, or a substituted or unsubstituted alkynyl group;

- - - - represents an optional double bond; for clarity the bond represented by - - - - may be present resulting in a double bond at the indicated position or it may be absent resulting in a single bond at the indicated position;

$R_1$ is a substituted or unsubstituted alkyl group or, a substituted or unsubstituted alkenyl group, a substituted or unsubstituted alkynyl group, or (CH$_2$)$_n$—R$_8$, where R$_8$ is a substituted or unsubstituted aryl, a substituted or unsubstituted aralkyl a substituted or unsubstituted heterocycle or a substituted or unsubstituted heterocycloalkyl;

$R_3$ is a protecting group;

$R_4$ is H, a substituted or unsubstituted alkyl, a substituted or unsubstituted aralalkyl, a substituted or unsubstituted heterocycloalkyl or a side chain group from any one of the naturally or non-naturally occurring amino acids; and n is an integer from 0-10.

Examples of various protecting groups are provided herein. In one embodiment, $R_3$ is a silyl ether, an alkyl ether, an alkoxymethyl ether, a tetrahydropyranyl ether, a methylthiomethyl ethers, an esters or a carbonate. In one embodiment, $R_3$ is an $OR_{10}$ group, wherein $R_{10}$ is a substituted or unsubstituted alkyl, a substituted or unsubstituted alkenyl group, a substituted or unsubstituted alkynyl group, a substituted or unsubstituted aryl, a substituted or unsubstituted aralkyl a substituted or unsubstituted heterocycle or a substituted or unsubstituted heterocycloalkyl. In a particular embodiment, when $R_{10}$ is a substituted or unsubstituted alkyl, a substituted or unsubstituted alkenyl group, a substituted or unsubstituted alkynyl group, such groups are from 1 to 6 carbons in length. In a particular embodiment, $R_3$ is an $O-CH_3$ group.

As discussed above, $R_4$ may be a side chain group from any one of the naturally or non-naturally occurring amino acids. As such the side group is defined to occupy the position R in the following structure In a specific embodiment, such side chain is selected from the group consisting of: $-CH_2(CH_2)_m(CH_3)(CH_3)$, $-CH(CH_3)(CH_2)_mCH3$, $-(CH_2)_mC(=O)(NH_2)$, $-(CH_2)_mCOOH$, $-(CH_2)_mSCH_3$, $-(CH_2)_mOH$, $-CH(OH)(CH_2)_mCH_3$, $-(CH_2)_mSH$, $CH_2(CH_2)_mNH_2$, and $-CH_2(CH_2)_mNHC(NH_2)(NH_2)$, wherein m is an integer selected from 1-4 for each occurrence.

In a specific embodiment, such side chain is selected from the group consisting of: $-CH_3$, $-CH(CH_3)(CH_3)$, $-CH_2CH_2(CH_3)(CH_3)$, $-CH(CH_3)CH_2CH_3$, $-CH_2C(=O)(NH_2)$, $-CH_2CH_2C(=O)(NH_2)$, $-CH_2COOH$, $-CH_2CH_2COOH$, $-CH_2CH_2SCH_3$, $-CH_2OH$, $-CH(OH)CH_3$, $-CH_2SH$, $-CH_2(CH_2)_3NH_2$, $-CH_2(CH_2)_2NHC(NH_2)(NH_2)$,

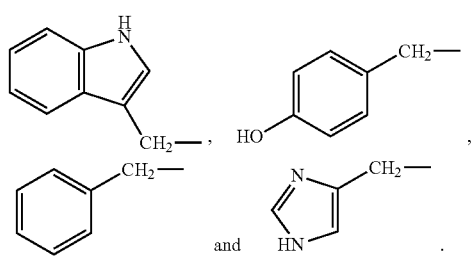

In a specific embodiment, such side chain is $-(CH_2)_mOH$, $-CH(OH)(CH_2)_mCH_3$, $-CH_2OH$ or $-CH(OH)CH_3$ wherein m is an integer selected from 1-4 for each occurrence.

In one embodiment of the foregoing, A is a ketone group and the compound has the formula IIa;

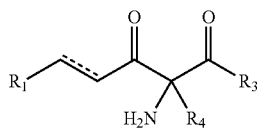

wherein:

$R_1$, $R_3$ and $R_4$ are as defined above for compounds of the formula II.

In one embodiment of the foregoing, A is $R_5$ and $R_6$, where $R_5$ is H and $R_6$ is OH and the compound has the formula IIb:

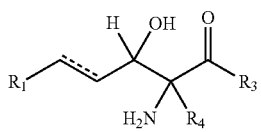

wherein:

$R_1$, $R_3$ and $R_4$ are as defined above for compounds of the formula II.

In a further embodiment, the compound of the formula II(b) may have the structures shown below as II(c)-II(e). In certain embodiments, compounds of the formula II(c) to II(e) are produced as intermediates in the synthesis of a sphingolipid.

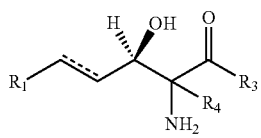

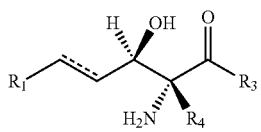

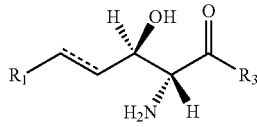

In a particular embodiment of the foregoing compound of the formula II, A is a ketone group, - - - - is present resulting in a double bond at the indicated position, $R_1$ is an unsubstituted $C_6$-$C_{14}$ alkyl, alkenyl or alkynyl group, $R_3$ is $O-CH_3$ and $R_4$ is H.

In another particular embodiment of the foregoing compound of the formula II, A is a ketone group, - - - - is absent resulting in a single bond at the indicated position, $R_1$ is an unsubstituted $C_6$-$C_{14}$ alkyl, alkenyl or alkynyl group, $R_3$ is $O-CH_3$ and $R_4$ is H.

In a particular embodiment of the foregoing compound of the formula II, A is a ketone group, - - - - is present resulting in a double bond at the indicated position, $R_1$ is a substituted $C_6$-$C_{14}$ alkyl, alkenyl or alkynyl group, $R_3$ is $O-CH_3$ and $R_4$ is H.

In another particular embodiment of the foregoing compound of the formula I, A is a ketone group, - - - - is absent resulting in a single bond at the indicated position, $R_1$ is a substituted $C_6$-$C_{14}$ alkyl, alkenyl or alkynyl group, $R_3$ is O—$CH_3$ and $R_4$ is H.

In a particular embodiment of the foregoing compound of the formula II, A is $R_5$ and $R_6$, where $R_5$ is H and $R_6$ is OH, - - - - is present resulting in a double bond at the indicated position, $R_1$ is an unsubstituted $C_6$-$C_{14}$ alkyl, alkenyl or alkynyl group, $R_3$ is O—$CH_3$ and $R_4$ is H.

In another particular embodiment of the foregoing compound of the formula II, A is $R_5$ and $R_6$, where $R_5$ is H and $R_6$ is OH, - - - - is absent resulting in a single bond at the indicated position, $R_1$ is an unsubstituted $C_6$-$C_{14}$ alkyl, alkenyl or alkynyl group, $R_3$ is O—$CH_3$ and $R_4$ is H.

In a particular embodiment of the foregoing compound of the formula I, A is $R_5$ and $R_6$, where $R_5$ is H and $R_6$ is OH, - - - - is present resulting in a double bond at the indicated position, $R_1$ is a substituted $C_6$-$C_{14}$ alkyl, alkenyl or alkynyl group, $R_3$ is O—$CH_3$ and $R_4$ is H.

In another particular embodiment of the foregoing compound of the formula I, A is $R_5$ and $R_6$, where $R_5$ is H and $R_6$ is OH, - - - - is absent resulting in a single bond at the indicated position, $R_1$ is a substituted $C_6$-$C_{14}$ alkyl, alkenyl or alkynyl group, $R_3$ is O—$CH_3$ and $R_4$ is H.

In another particular embodiment of the foregoing compound of the formula I, A is a ketone group, - - - - is present resulting in a double bond at the indicated position, $R_1$ is an unsubstituted $C_6$-$C_{14}$ alkyl, alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is present resulting in a double bond at the indicated position, $R_1$ is a substituted $C_6$-$C_{14}$ alkyl or alkenyl or alkynyl group; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is absent resulting in a single bond at the indicated position, $R_1$ is an unsubstituted $C_6$-$C_{14}$ alkyl, alkenyl or alkynyl; $R_2$ is $CH_3$ or benzyl, $R_3$ is O—$CH_3$ and $R_4$ is $CH_2$—OH.

In another particular embodiment of the foregoing compound of the formula I, A is a ketone group, - - - - is absent resulting in a single bond at the indicated position, $R_1$ is a substituted $C_6$-$C_{14}$ alkyl, alkenyl or alkynyl; $R_2$ is $CH_3$ or benzyl, $R_3$ is O—$CH_3$ and $R_4$ is $CH_2$—OH.

In a particular embodiment of the foregoing compound of the formula II, A is $R_5$ and $R_6$, where $R_5$ is H and $R_6$ is OH, - - - - is present resulting in a double bond at the indicated position, $R_1$ is an unsubstituted $C_6$-$C_{14}$ alkyl, alkenyl or alkynyl group, $R_3$ is O—$CH_3$ and $R_4$ is $CH_2$—OH.

In another particular embodiment of the foregoing compound of the formula II, A is $R_5$ and $R_6$, where $R_5$ is H and $R_6$ is OH, - - - - is absent resulting in a single bond at the indicated position, $R_1$ is an unsubstituted $C_6$-$C_{14}$ alkyl, alkenyl or alkynyl group, $R_3$ is O—$CH_3$ and $R_4$ is $CH_2$—OH.

In a particular embodiment of the foregoing compound of the formula I, A is $R_5$ and $R_6$, where $R_5$ is H and $R_6$ is OH, - - - - is present resulting in a double bond at the indicated position, $R_1$ is a substituted $C_6$-$C_{14}$ alkyl, alkenyl or alkynyl group, $R_3$ is O—$CH_3$ and $R_4$ is $CH_2$—OH.

In another particular embodiment of the foregoing compound of the formula I, A is $R_5$ and $R_6$, where $R_5$ is H and $R_6$ is OH, - - - - is absent resulting in a single bond at the indicated position, $R_1$ is a substituted $C_6$-$C_{14}$ alkyl, alkenyl or alkynyl group, $R_3$ is O—$CH_3$ and $R_4$ is $CH_2$—OH.

In one embodiment of the foregoing, $R_1$ is an unsubstituted $C_{10}$ alkyl group, $R_1$ is an unsubstituted $C_{11}$ alkyl group, $R$, is an unsubstituted $C_{12}$ alkyl group or $R_1$ is an unsubstituted $C_{13}$ alkyl group.

In one embodiment of the foregoing, $R_1$ is a substituted $C_{10}$ alkyl group. $R_1$ is a substituted $C_{11}$ alkyl group, $R_1$ is substituted $C_{12}$ alkyl group or $R_1$ is a substituted $C_{13}$ alkyl group.

In one embodiment of the foregoing, when a group, such as $R_1$, is a substituted alkyl group, alkenyl group or alkynyl group, the substituents for substitution include those listed herein with regard to the definition of a substituted alkyl group. In a particular embodiment, the substituents for substitution are —OH, —$NH_2$, $N_3$ or =O. When such group is substituted the number of substituent groups may vary from one to the number of carbon atoms in the substituted alkyl chain. In one embodiment, the number of substituent groups is from 1-6; in another embodiment, the number of substituent groups is from 1-8; in another embodiment, the number of substituent groups is from 1-4, in another embodiment, the number of substituent groups is from 1-2.

In one embodiment of the foregoing, when $R_1$ is a substituted or unsubstituted alkenyl group or alkynyl group, such group may have from 1-6 double or triple bonds. In one embodiment, such group has from 1-4 double or triple bonds; in another embodiment, such group has from 1-2 double or triple bonds; in another embodiment, such group has 1 double or triple bond. The double bonds may be in the cis or trans configuration. When multiple double bonds are present, the double bonds may be all cis, all trans or a combination of cis and trans. In one embodiment, when multiple double bonds are present, the double bonds are all cis or all trans.

General Synthetic Scheme

Compounds of the general formula I and II may be synthesized by a number of methods known in the art. The following is a general synthetic scheme that may be used to produce compounds of the general formula I and II. The disclosed scheme is provided as an exemplary embodiment only and should not be construed to limit the synthetic methods that may be used to manufacture compounds of the general formula I and II to the methods disclosed below.

In the schemes that follow $R_1$, $R_2$ and $R_3$ may be the groups as defined above in the definition of the compounds of the general formula I (as protected by the appropriate protecting groups described herein).

In a first step (scheme 1a), an aldehyde containing compound (1), such as, but not limited to dodecanal, is reacted with a dicarboxylic acid in the presence of pyridine to form a corresponding acid (2). After neutralization, extraction with a polar solvent and washing, the compound 2 may be recovered by conventional means, such as by recrystallization.

scheme 1a

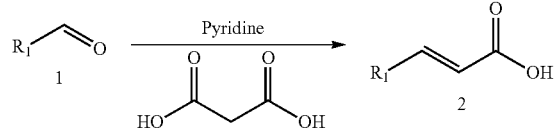

In scheme 1b, the product 2 is reacted with a chloride donor in the presence of an organic solvent to produce the corresponding acid chloride (3). The product (3) may be used without further purification if desired.

scheme 1b

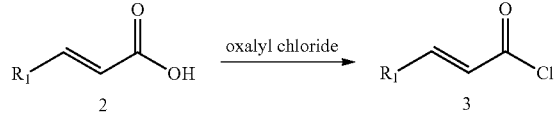

In scheme 1c, the product 3 is reacted with a Cbz-amino acid-methyl ester, such as Cbz glycine methyl ester in an organic solvent in the presence of a catalysts, such as lithium bis(trimethylsilyl)amide, to yield the compound 4. The crude product is extracted, washed dried and purified by conventional means, such as column chromatography.

scheme 1c

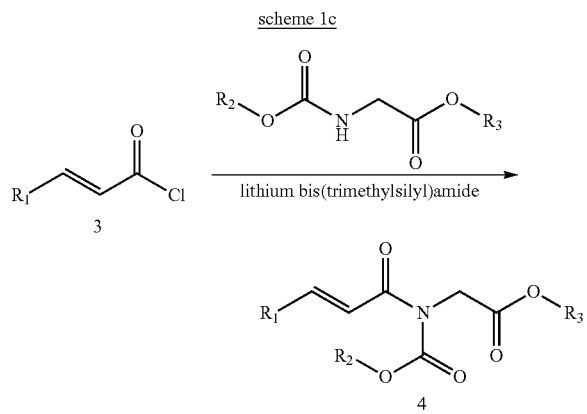

In scheme 1d, the product 4 is reacted with a hexamethylphosphoramide in the an organic solvent in the presence of a catalysts, such as lithium bis(trimethylsilyl)amide, to yield the final product 5. The crude product is extracted, washed dried and purified by conventional means, such as column chromatography.

scheme 1d

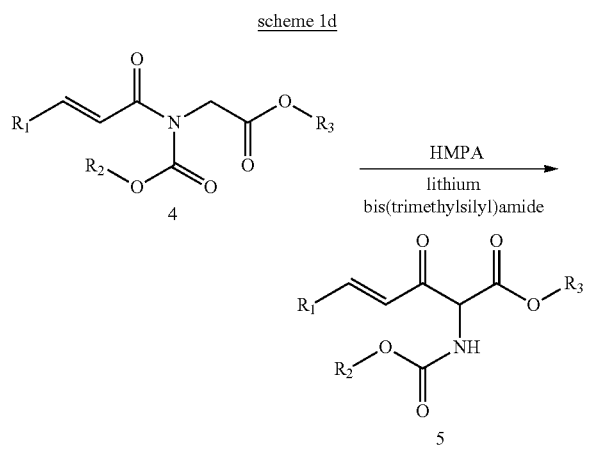

If desired, the double bond may be reduced by methods known in the art, such as but not limited to hydrogenation, to yield the product 6.

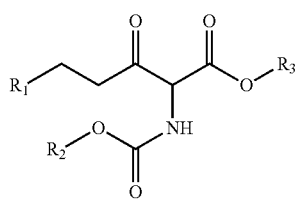

Overall, the reaction may be represented as shown in scheme 1 below.

Scheme 1.

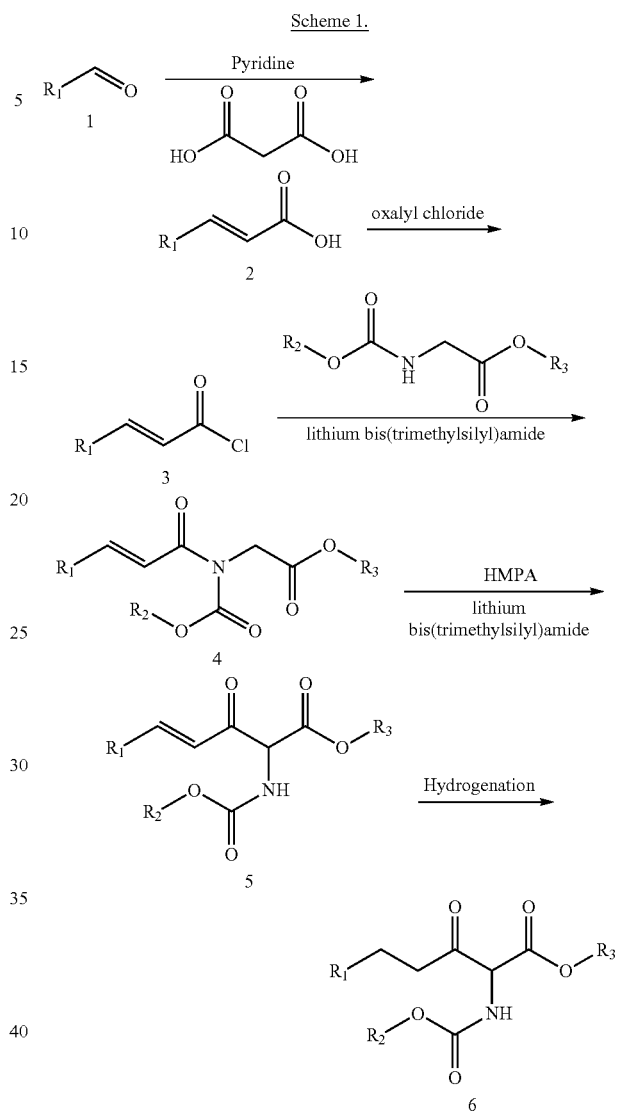

The final products 5 or 6, after deprotection, may be used as described herein. In a particular embodiment, such compounds are used in the synthesis of a sphingolipid or are produced as intermediates during the manufacture a sphingolipid. In one embodiment, the sphingolipid is sphingosine. In an alternate embodiment, the sphingolipid is a compound incorporating sphingosine or a compound that uses sphingosine as starting material or an intermediate in its synthesis. In one embodiment, such compounds include, but are not limited to, sphingosine-1-P, ceramides, gangliosides and sphigomyelin.

The general approach above may also be used to produce a sphingofugin or other inhibitors of sphingosine synthesis. A general approach to such a synthesis is provided in Scheme 2 below. As above, $R_1$, $R_2$ and $R_3$ may be the groups as defined above in the definition of the compounds of the general formula I (as protected by the appropriate protecting groups described herein) and $R_{12}$ may be a group as defined in $R_4$ as defined above in the definition of the compounds of the general formula I (as protected by the appropriate protecting groups described herein). The overall steps are similar to those described in Scheme 1 above. In Scheme 2, the lithium bis(trimethylsilyl)amide reagent is modified to contain an additional group in order to introduce the R4 functionality. Furthermore, scheme 2 utilizes a reducing agent to reduce one of the ketone groups to a hydroxyl group in the final product. The final product may be used as described herein. In a particular embodiment, such compounds are used in the synthesis of a sphingofugin or are produced as intermediates during the manufacture a sphingofugin.

Scheme 2

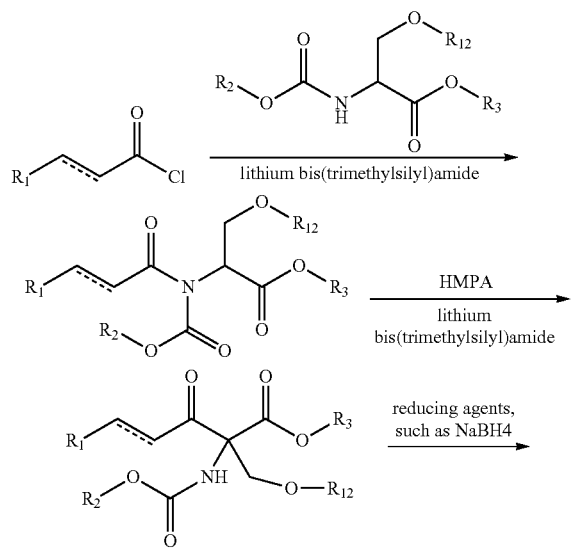

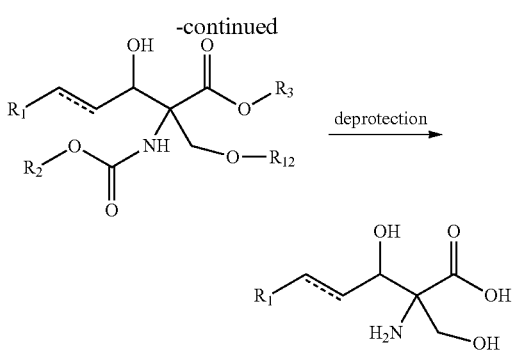

Use of Compounds of the Formula I and II

In one embodiment, compounds of the formula I and II can be used in the manufacture of certain lipids or are produced as intermediates during the manufacture of certain lipids. In one aspect, the lipid is a sphingolipid. Therefore, in a particular embodiment, compounds of the formula I and II can be used in the manufacture of a sphingolipid or are produced as intermediates during the manufacture a sphingolipid. In one embodiment, the sphingolipid is sphingosine, including specific enantiomeric forms of sphingosine (such as but not limited to 2S, 3R sphingosine). In an alternate embodiment, the sphingolipid is a compound incorporating sphingosine or a compound that uses sphingosine as starting material or as an intermediate in its synthesis. In one embodiment, such compounds include, but are not limited to, sphingosine-1-P, ceramides, gangliosides and sphingomyelin. Exemplary structures for sphingosine, 2S, 3R sphingosine, sphingosine-1-P, ceramide, gangliosides and sphingomyelin are provided below.

Check Stereochemistry of Structures

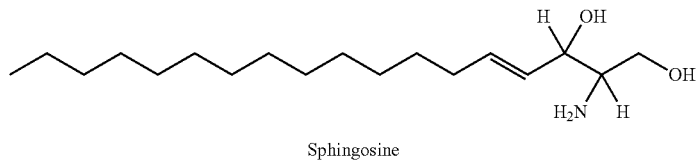

Sphingosine

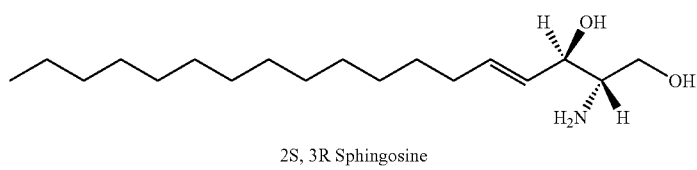

2S, 3R Sphingosine

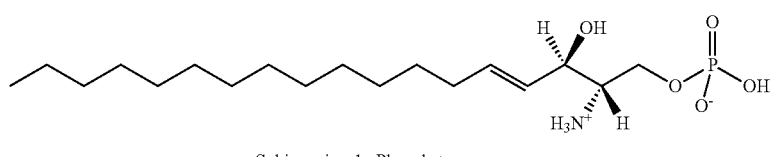

Sphingosine-1--Phosphate

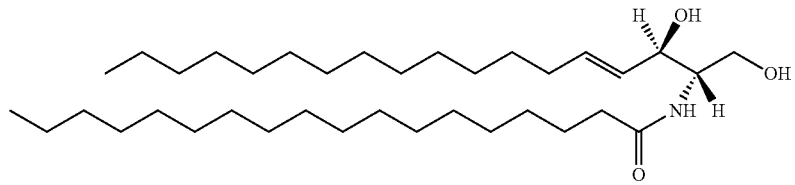

Ceramide (Porcine Brain)

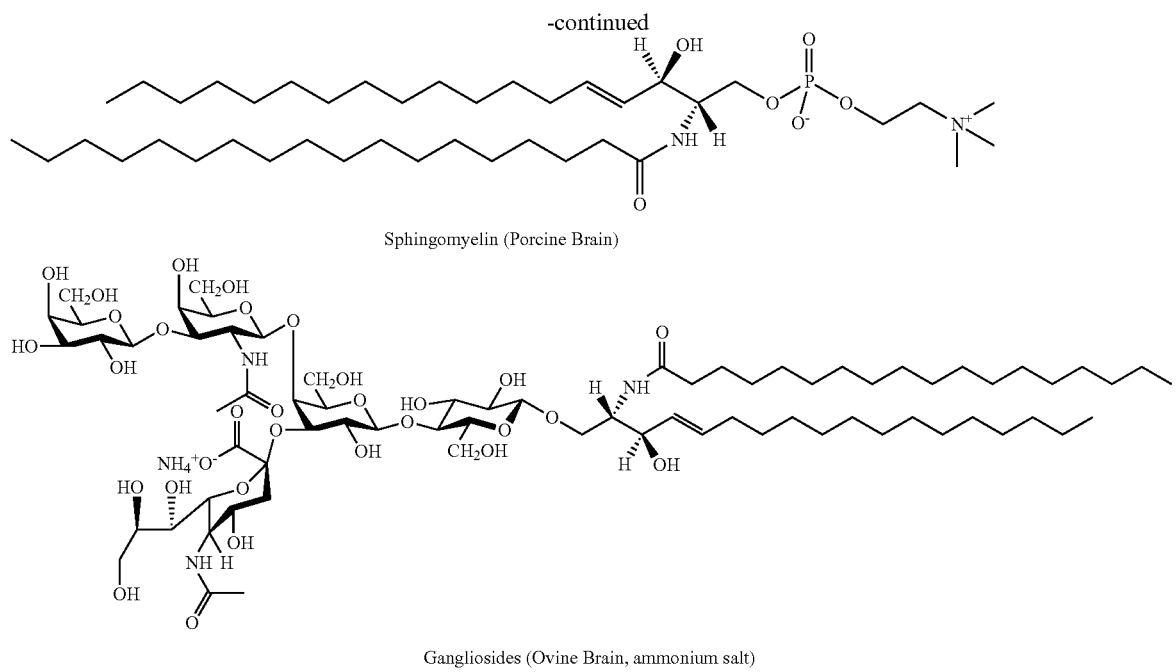

Sphingomyelin (Porcine Brain)

Gangliosides (Ovine Brain, ammonium salt)

In another embodiment, compounds of the formula I and II can be used in the manufacture of inhibitors of lipid synthesis. In one aspect, the lipid is a sphingolipid. Therefore, in a particular embodiment, compounds of the formula I and II can be used in the manufacture of an inhibitor of sphingolipid synthesis. In a particular embodiment, the compound is a sphingofugin. The structure of an exemplary sphingofugin, including a specific enatomeric form, is provided below.

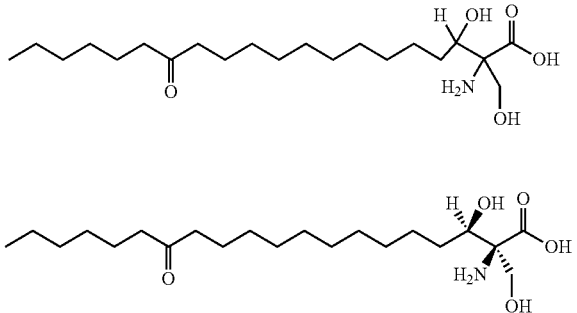 [SMILES: CCCCCCC(=O)CCCCCCCCCCC(O)C(N)(CO)C(=O)O ; CCCCCCC(=O)CCCCCCCCCC[C@@H](O)[C@@](N)(CO)C(=O)O]

Methods of Manufacture

The present disclosure also provides for methods of manufacturing a certain lipids. In one embodiment, the method of manufacture comprise providing a compound of the general formula I, performing a series of chemical transformations on the compound of the general formula I to arrive at a sphingolipid. Exemplary chemical transformations include, but are not limited to, transformations that produce a stereoselective arrangement of groups at the indicated positions (illustrated with respect to a compound of the formula I, but applicable to all compounds of the general formula I and II). In a particular embodiment, such chemical transformations involve an enzymatic step where the enzyme is responsible, at least in part, for the stereoselective arrangement.

In one embodiment, the method of manufacture comprise providing a compound of the general formula II, performing a series of chemical transformations on the compound of the general formula II to arrive at a sphingolipid. Exemplary chemical transformations include, but are not limited to, transformations that produce a stereoselective arrangement of groups at the indicated positions above. In a particular embodiment, such chemical transformations involve an enzymatic step where the enzyme is responsible, at least in part, for the stereoselective arrangement.

In one embodiment of the foregoing methods, the sphingolipid is sphingosine, including specific enantiomeric forms of sphingosine (such as but not limited to 2S, 3R sphingosine). In another particular embodiment, the sphingolipid is a compound incorporating sphingosine or a compound that uses sphingosine as starting material or uses sphingosine as an intermediate in its synthesis. In one embodiment, such compounds include, but are not limited to, sphingosine-1-P, ceramides, gangliosides and sphigomyelin. In another particular embodiment, the sphingolipid is an inhibitor of sphingosine synthesis, such as, but not limited to, a sphingofugin.

EXAMPLES

Example 1

Synthesis of (E)-methyl 2-((benzyloxy)carbonyl) amino)-3-oxohexadec-4-enoate

1) Synthesis of (E)-tetradec-2-enoic acid

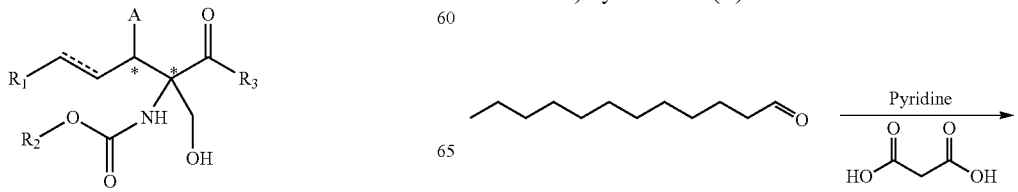

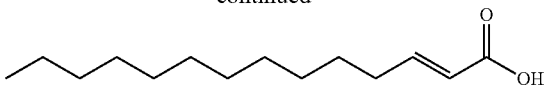

To a dry flask containing malonic acid (56.5 g) and pyridine (132 ml) was added dodecanal (100 g) dropwise to maintain the internal temperature under 35° C. under nitrogen atmosphere while stirring. After the addition, piperidine (4 ml) was added. The reaction mixture was then heated to 55° C. for 1 hr and 90° C. for 3 hrs. The mixture was cooled to room temperature and poured into ice-water (~1 L). After the addition of 400 ml 6M HCl, the mixture was extracted with ethyl acetate (2 L). The ethyl acetate phase was washed with DI water twice. The solvent was removed under vacuum. The crude product was crystallized from hexane. The pure product was obtained as a white solid (80.5 g, 65.6% yield). Proton NMR(CDCl3) δ 0.88 (t, 3H), 1.26 (m, 16H), 1.45 (m, 2H), 2.22 (m, 2H), 5.82 (td, 1H), 7.09 (td, 1H).

2) Synthesis of (E)-tetradec-2-enoyl chloride

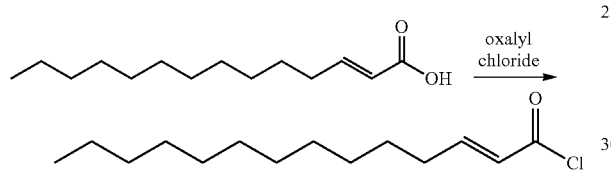

(E)-tetradec-2-enoic acid (18.7 g) was dissolved in anhydrous dichloromethane (200 ml) under nitrogen with stirring. The solution was cooled in ice-water bath for 30 min. Oxalyl chloride (9.1 ml) was added dropwise. The reaction mixture was slowly warm up to room temperature overnight. The solvent was removed under vacuum. The product was obtained as clear oil (20.0 g, 99%) and used in next step synthesis without further purification.

3) Synthesis of (E)-methyl 2-(N-((benzyloxy)carbonyl)tetradec-2-enamido)acetate

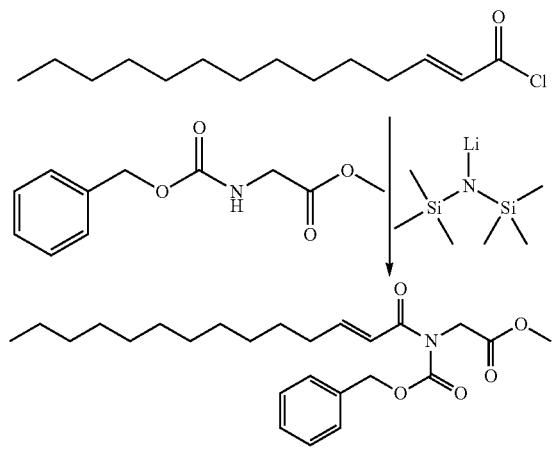

A solution of lithium bis(trimethylsilyl)amide (44.8 ml, 1M solution) in anhydrous THF (50 ml) was cooled to −70° C. under argon in a dry flask with stirring. To the solution was added Cbz glycine methyl ester (10.0 g) in THF (20 mL) dropwise while maintaining the reaction temperature at −70° C. After 30 min stirring at −70° C., a solution of the (E)-tetradec-2-enoyl chloride (12.1 g) in THF (10 mL) was added slowly at −70° C. The reaction mixture was stirred at −70° C. for 1 hr and then allowed to warm up to 0° C. The reaction was quenched with aqueous citric acid solution (5%, 300 ml) and warmed up to room temperature. The crude product was extracted with ethyl acetate (500 ml). The ethyl acetate phase was washed with DI water twice and dried with sodium sulfate. The solvent was removed under vacuum to yield oily residue, which was purified by silica gel column chromatography. Pure product was obtained after column purification as a clear oil (12.8 g, 66.2% yield). Proton NMR(CDCl3) δ 0.88 (t, 3H), 1.26 (m, 16H), 1.43 (m, 2H), 2.22 (m, 2H), 3.67 (s, 3H), 4.53 (s, 2H), 5.24 (s, 2H), 6.94 (d, 1H), 7.05 (td, 1H). 7.36 (m, 5H).

4) Synthesis of (E)-methyl 2-(((benzyloxy)carbonyl)amino)-3-oxohexadec-4-enoate

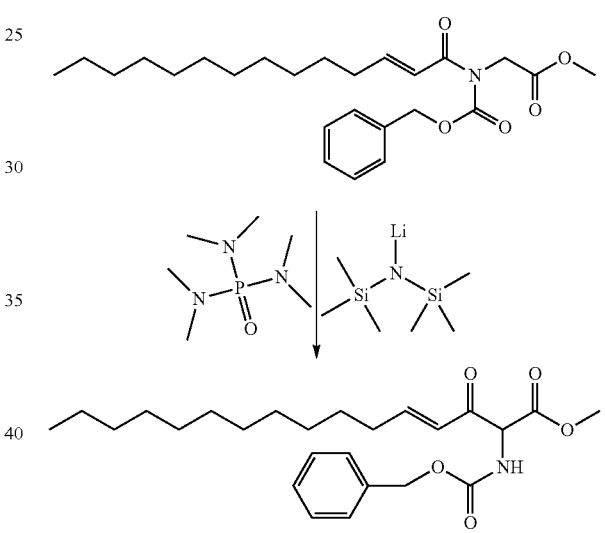

A solution of lithium bis(trimethylsilyl)amide (86.0 ml, 1M solution) in anhydrous THF (100 ml) was cooled to −70° C. under argon in a dry flask with stirring. To the solution was added hexamethylphosphoramide (HMPA, 12.4 ml) and E)-methyl 2-(N-((benzyloxy)carbonyl)tetradec-2-enamido) acetate (15.4 g) in THF (20 mL) dropwise while maintaining the reaction temperature at −70° C. The reaction mixture was stirred at −70° C. for 2.5 hr and then quenched with aqueous citric acid solution (5%, 500 ml). After warm up to room temperature, the crude product was extracted with ethyl acetate (500 ml). The ethyl acetate phase was washed with DI water twice and dried with sodium sulfate. The solvent was removed under vacuum to yield oily residue, which was purified by silica gel column chromatography. Pure product was obtained after column purification as a white solid (13.1 g, 85% yield). Proton NMR(CDCl3) δ 0.88 (t, 3H), 1.26 (m, 16H), 1.45 (m, 2H), 2.21 (m, 2H), 3.65 (s, 0.6H), 3.78 (s, 2.3H), 3.81 (s, 0.1H), 5.16 (m, 2H), 5.37 (s, 0.1H), 5.58 (s, 0.3H), 6.10 (d, 0.5H), 6.77 (m, 0.4H), 7.18 (m, 0.6H). 7.36 (m, 5H). MS (m/z, positive); 432.7 (M+H), 449.6 (M+NH4).

Note: Complex NMR peak pattern was due to the existence of various enolization forms.

What is claimed:

1. A compound of the general formula I:

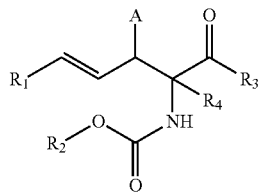

wherein:
A is a ketone (=O);
$R_1$ is a substituted or unsubstituted alkyl group or, a substituted or unsubstituted alkenyl group, or a substituted or unsubstituted alkynyl group wherein the alkyl, alkenyl and alkynyl groups are C6-C18;
$R_2$ is H, substituted or unsubstituted alkyl group or, a substituted or unsubstituted alkenyl group, a substituted or unsubstituted alkynyl group, benzyl, or $(CH_2)_p$—$R_9$;
$R_3$ is a protecting group;
$R_4$ is H, a substituted or unsubstituted alkyl, a substituted or unsubstituted aralalkyl, a substituted or unsubstituted heterocycloalkyl or a side chain group from any one of the naturally or non-naturally occurring amino acids;
$R_9$ is selected from a substituted or unsubstituted aryl, a substituted or unsubstituted aralkyl a substituted or unsubstituted heterocycle or a substituted or unsubstituted heterocycloalkyl; and
p is selected from 0-10.

2. The compound of claim 1, wherein $R_3$ is a silyl ether, an alkyl ether, an alkoxymethyl ether, a tetrahydropyranyl ether, a methylthiomethyl ethers, an esters or a carbonate.

3. The compound of claim 1, wherein $R_3$ is $OR_{10}$, wherein $R_{10}$ is a substituted or unsubstituted alkyl, a substituted or unsubstituted alkenyl group, a substituted or unsubstituted alkynyl group, a substituted or unsubstituted aryl, a substituted or unsubstituted aralkyl a substituted or unsubstituted heterocycle or a substituted or unsubstituted heterocycloalkyl.

4. The compound of claim 1, wherein $R_3$ is $OR_{10}$, wherein $R_{10}$ is a substituted or unsubstituted alkyl, a substituted or unsubstituted alkenyl group, or a substituted or unsubstituted alkynyl group.

5. The compound of claim 1, wherein $R_3$ is an O—$CH_3$ group or a benzyl group.

6. The compound of claim 1, wherein $R_4$ is selected from the group consisting of: H,
—$CH_2(CH_2)_m(CH_3)(CH_3)$, —$CH(CH_3)(CH2)_mCH3$, —$(CH_2)_mC(=O)(NH_2)$, —$(CH_2)_mCOOH$, —$(CH_2)_mSCH_3$, —$(CH_2)_mOH$, —$CH(OH)(CH_2)_mCH_3$, —$(CH_2)_mSH$, $CH_2(CH_2)_mNH_2$, and —$CH_2(CH_2)_mNHC(NH_2)(NH_2)$, wherein m is an integer selected from 1-4 for each occurrence.

7. The compound of claim 1, wherein $R_4$ is selected from the group consisting of: H,
—$CH_3$, —$CH(CH_3)(CH_3)$, —$CH_2CH_2(CH_3)(CH_3)$, —$CH(CH_3)CH_2CH_3$, —$CH_2C(=O)(NH_2)$, —$CH_2CH_2C(=O)(NH_2)$, —$CH_2COOH$, —$CH_2CH_2COOH$, —$CH_2CH_2SCH_3$, —$CH_2OH$, —$CH(OH)CH_3$, —$CH_2SH$, —$CH_2(CH_2)_3NH_2$, —$CH_2(CH_2)_2NHC(NH_2)(NH_2)$,

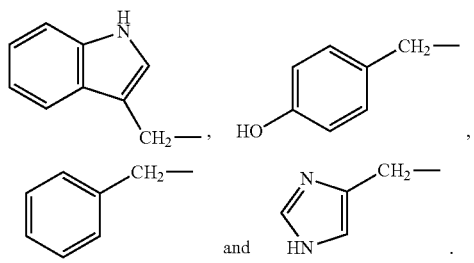

and

8. The compound of claim 1, wherein $R_4$ is H, —$(CH_2)_mOH$, —$CH(OH)(CH_2)_mCH_3$, —$CH_2OH$ or —$CH(OH)CH_3$, wherein m is an integer selected from 1-4 for each occurrence.

9. The compound of claim 1, wherein $R_1$ contains from 1 to 6 substitutions.

10. The compound of claim 1, wherein the substituents on $R_1$ are independently selected from —OH, —$NH_2$, —$N_3$ or =O.

11. The compound of claim 1, wherein $R_1$ contains from 1-6 double and/or triple bonds.

12. The compound of claim 1, wherein A is a ketone group, - - - - is present, $R_1$ is an unsubstituted or substituted $C_6$-$C_{14}$ alkyl, alkenyl or alkynyl group, $R_2$ is $CH_3$ or benzyl; $R_3$ is O—$CH_3$ and $R_4$ is H or $CH_2$—OH.

13. The compound of claim 1, wherein A is a ketone group, - - - - is absent, $R_1$ is an unsubstituted or substituted $C_6$-$C_{14}$ alkyl, alkenyl or alkynyl group, $R_2$ is $CH_3$ or benzyl, $R_3$ is O—$CH_3$ and $R_4$ is H or $CH_2$—OH.

14. The compound of claim 1, wherein the compound has the a structure selected from the group consisting of:

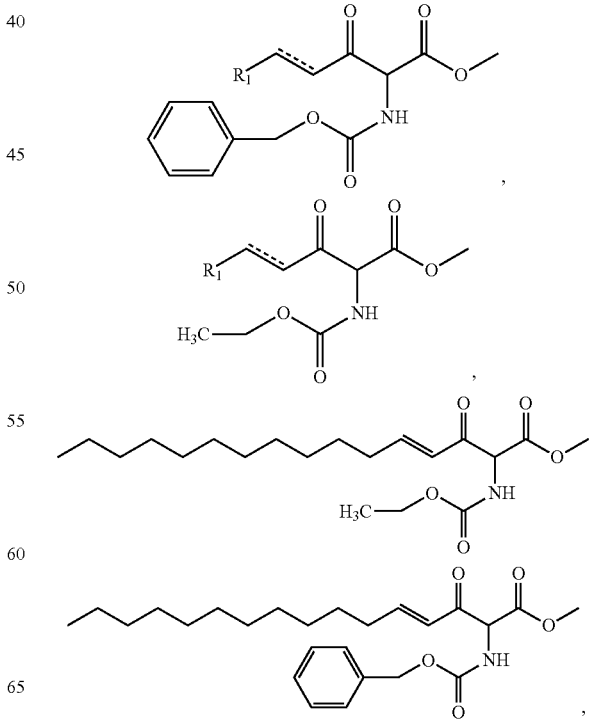

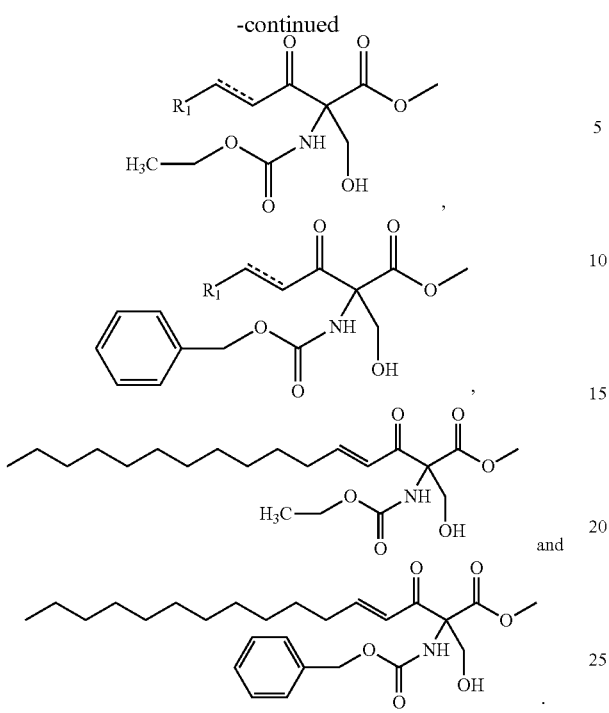
15. The compound of claim 1, wherein the compound is used in the synthesis of a sphingolipid.
16. The compound of claim 1, wherein the compound is used in the synthesis of a sphingosine.
* * * * *